(12) United States Patent
Tombuelt-Meyer et al.

(10) Patent No.: US 9,006,366 B2
(45) Date of Patent: Apr. 14, 2015

(54) PROCESSES USING SUPERCRITICAL MEDIUM TO PRODUCE POLYMERS

(75) Inventors: Thomas Tombuelt-Meyer, Nettersheim (DE); Axel Meyer, Schwalbach (DE); Torsten Lindner, Kronberg (DE)

(73) Assignee: The Procter & Gamble Company, Cincinnati, OH (US)

(*) Notice: Subject to any disclaimer, the term of this patent is extended or adjusted under 35 U.S.C. 154(b) by 741 days.

(21) Appl. No.: 13/285,058

(22) Filed: Oct. 31, 2011

(65) Prior Publication Data
US 2012/0108687 A1    May 3, 2012

(30) Foreign Application Priority Data

Nov. 1, 2010  (EP) .................................... 10189538

(51) Int. Cl.
| | | |
|---|---|---|
| *C08F 2/06* | (2006.01) | |
| *C08F 20/06* | (2006.01) | |
| *C08F 220/06* | (2006.01) | |
| *A61L 15/60* | (2006.01) | |
| *C08J 3/24* | (2006.01) | |

(52) U.S. Cl.
CPC ............... *C08F 220/06* (2013.01); *A61L 15/60* (2013.01); *C08J 3/245* (2013.01); *C08J 2333/02* (2013.01)

(58) Field of Classification Search
USPC ....................................................... 526/317.1
See application file for complete search history.

(56) References Cited

U.S. PATENT DOCUMENTS

| 4,748,220 A | * | 5/1988 | Hartmann et al. ............... 526/89 |
| 7,871,640 B2 | * | 1/2011 | Flohr et al. .................... 424/443 |
| 2010/0068520 A1 | | 3/2010 | Stueven |

FOREIGN PATENT DOCUMENTS

WO         WO 00/05273         3/2000

OTHER PUBLICATIONS

Xu et al. Polymer, 2001, 42, 1369-1373.*
Tao Liu et al. Polymer 2006, 47, 4276-4281.*
PhD Thesis by Tao Liu (North Carolina State University, 2005).*
International Search Report, PCT/US2011/058207, mailed Dec. 7, 2011, 13 pages.
Liu, "Continuous Precipitation Polymerization of Acrylic Acid in Supercritical Carbon Dioxide", 2005, 191 pages.
Liu, et al., "Cross-Linking Polymerization of Acrylic Acid in Supercritical Carbon Dioxide", May 31, 2006, 6 pages.
EP International Search Report dated Mar. 11, 2014 (7 pages).

* cited by examiner

*Primary Examiner* — Vu A Nguyen
(74) *Attorney, Agent, or Firm* — Andrew J. Mueller; Andrew A. Paul; Richard L. Alexander

(57) ABSTRACT

Processes for making water-absorbent cross-linked polymers, such as polyacrylic acids/polyacrylates, using supercritical medium; and water-absorbent polymers, e.g. particles thereof, obtained by such processes, where such particles may be porous.

19 Claims, No Drawings

PROCESSES USING SUPERCRITICAL MEDIUM TO PRODUCE POLYMERS

FIELD OF THE INVENTION

This invention relates to processes for making water-absorbent cross-linked polymers, such as polyacrylic acids/polyacrylates, using supercritical medium for monomer solution and for the reactions. This invention also relates to water-absorbent polymers obtained by such processes, e.g. particles thereof that may be porous.

BACKGROUND OF THE INVENTION

An important component of disposable absorbent articles, such as diapers, is an absorbent core structure comprising water-absorbing polymers, e.g. hydrogel-forming water-swellable polymers, also referred to as absorbent gelling material (AGM), or super-absorbent polymers (SAP's). This polymer material ensures that large amounts of bodily fluids, e.g. urine, can be absorbed by the article during its use and locked away, thus providing low rewet and good skin dryness.

Especially useful water-swellable polymers or SAP's are often made by initially polymerizing unsaturated carboxylic acids or derivatives thereof, such as acrylic acid, alkali metal (e.g., sodium and/or potassium) or ammonium salts of acrylic acid, alkyl acrylates, and the like in the presence of cross-linking compounds, such as (relatively small amounts of) di- or poly-functional monomers such as N,N'-methylenebisacrylamide, trimethylolpropane triacrylate, ethylene glycol di(meth)acrylate, or triallylamine. The di- or poly-functional monomer materials serve to cross-link the polymer chains thereby rendering them water-insoluble, yet water-swellable. These cross-linked absorbent polymers contain a multiplicity of carboxylate groups attached to the polymer backbone. It is generally believed, that the neutralized carboxylate groups generate an osmotic driving force for the absorption of body fluids by the cross-linked polymer network.

Such reactions are typically done with aqueous solutions of the monomers, resulting cross-linked polymers that have absorbed water (they are typically swollen hydrogels). The water is then subsequently removed from these materials, to render dry particulate water-absorbing (swellable) polymers. The removal of water is an energy-consuming process. Hence, there is a desire to provide less energy consuming processes.

One proposed route would be to use less water during the production of the water-absorbing cross-linked polymers. However, the inventors found that when highly concentrated monomer solutions are used, the resulting polymers may be more physically entangled, which can negatively impact the performance. Additionally, the reaction often is so exothermic that high monomer concentrations could lead to explosions.

Furthermore, and in contrast, the inventors found that it may be beneficial to use less concentrated monomer solutions, to obtain less entangled (e.g. more linear polymers) water-absorbing cross-linked polymers. However, this would require an even more energy intensive drying process.

The inventors have now found a method for producing water-absorbing cross-linked polymers, such as cross-linked polyacrylic acids/polyacrylates using a supercritical medium, including or consisting of, for example, supercritical carbon dioxide, that can be easily removed, e.g. by pressure reduction. This method can reduce the energy consumption associated with the removal of large amounts of water, and it can provide water-absorbing cross-linked polymers, e.g. in particulate form, that can even be made porous, to improve the rate of absorption of fluids, such as urine and blood, and that can be effectively used in absorbent articles.

SUMMARY OF THE INVENTION

This invention relates to processes for making water-absorbent cross-linked polymers, such as polyacrylic acids/polyacrylates, using supercritical material as medium for the monomers and as medium for the polymerization and cross-linking reaction. This invention also relates to water-absorbent polymers obtained by such processes, and particles thereof that, e.g., may be porous.

In recent years, supercritical fluids, and in particular, supercritical carbon dioxide, has been employed in various extraction processes and it has been proposed for polymer synthesis. The inventors now found that it can be used to make water-absorbing cross-linked polymers suitable for absorbent articles (such as diapers).

In a first aspect of the invention, a process for making water-absorbing cross-linked polymers is provided, said process comprising the steps of:
  a) obtaining polymerizable monomers;
  b) obtaining a supercritical (reaction) medium;
  c) obtaining a polymerization initiator system;
  d) obtaining a cross-linking system;
  e) obtaining optionally a neutralizing system;
  f) combining the polymerizable monomers of a) and said supercritical reaction medium of b) and a polymerization initiator of c) and said cross-linking compound of d), and optionally neutralizing agent to form a mixture; thereby
  g) polymerizing said polymerizable monomers to form polymers and cross-linking said polymers, to form water-absorbing cross-linked polymers;
  and for example: i) separating said medium from said water-absorbing cross-linked polymers, e.g. said medium is made into a gas and removed; the process may then comprise the step of: preferably submitting said gas (or: gaseous phase) to an increased pressure to form a supercritical fluid or medium and recycling it to a subsequent step b).

The combination of the components in step f) may be done simultaneously, i.e. as a single step, or as multiple subsequent steps, in any order. For example, the initiator system may be added at last.

The process may be such that said step g), or step f) and g) are done in a first reactor or reactor section with a first pressure, and said process comprises the additional steps of:
  h) transferring said the water-absorbing cross-linked polymers and supercritical medium of step g) to a second reactor or second reactor portion that has a second, reduced pressure to obtain water-absorbing cross-linked polymers, preferably in particulate form, and gaseous phase of said supercritical medium, or part thereof; and
  i) separating said gaseous phase from said water-absorbing cross-linked polymers, and preferably submitting said gaseous phase to an increased pressure to form a supercritical fluid or medium and recycling it to a subsequent step b).

In addition, or alternatively, the process may be such that said step f) is done in a first reactor or first reactor section with a first pressure, preferably without the presence of said polymerization initiator system, and said process comprises the additional steps of:
  transferring said mixture of step f) to a second reactor or second reactor section, and preferably simultaneously adding the polymerization initiator system c), said second reactor or second reactor section having a second, reduced pressure, to thereby perform step g) to obtain water-absorbing cross-linked polymers, preferably in particulate form, and to thereby obtain a gaseous phase of said supercritical medium, or part thereof; and i) separating said gaseous phase from said water-absorbing cross-linked polymers, and preferably submitting said gaseous phase to an increased pressure to form a supercritical fluid or medium and recycling it to a subsequent step b).

Said second pressure is reduced compared to said first pressure, e.g. said second pressure being for example ambient pressure, to obtain water-absorbing cross-linked polymers and gaseous phase of said supercritical medium, or part thereof for example, a tube reactor may be used with two or more sections.

The process can be done at any temperature and pressure at which the supercritical state of the medium is achieved and/or maintained and the desired reaction can take place.

In some embodiments herein, the supercritical (reaction) medium comprises a supercritical primary medium, for example supercritical carbon dioxide ($CO_2$), and one or more other secondary mediums, e.g. liquids, which may be one or more additional supercritical secondary medium (or media) and/or which may be liquids that are not in supercritical state, but are mixed with said primary supercritical medium; for example to aid solution of monomer salts, neutralization salts etc; such secondary medium (media) may be a polar medium (media), including (supercritical) water, (supercritical) alcohol (methanol), (supercritical) ketone (acetone), and mixtures thereof. In some embodiments the supercritical medium may consist of supercritical carbon dioxide ($CO_2$).

The process can be done at reduced (less energy consuming) temperatures, e.g. from 35° C., or preferably from 40° C., or for example from 50° C., to for example up to 130° C. or up to 120° C.; and for example at a pressure of at least 50 bar, or at least 80 bar. When the supercritical medium comprises or is $CO_2$, the temperate may for example from 35° C., or 40° C., or 50° C., and the pressure may for example be 80 bar or more, or for example 120 bar or more, or for example less than 250 bar.

Furthermore, the inventors found that this process can be used to create water-absorbing cross-linked polymer particles that have pores or channels, formed by fast evaporating supercritical medium (fluid) that can provide faster liquid transport into the particles (faster absorption).

Furthermore, the inventors found that this process can be done by the use of nozzles or spray heads with specific orifice dimensions and process settings, resulting in polymer particles of specific particle sizes (and within narrow range).

In some embodiment herein, the water-absorbing cross-linked polymers are in particulate form, which may be any particulate form, including spherical particles, or sausage shaped particles, or ellipsoid shaped particles.

In some embodiments herein, the weight ratio of said polymerizable monomers to said supercritical medium, or for example to said supercritical carbon-dioxide, is less than 1:1, or less than 2:5, or less than 1:2 or less than 1:3.

In another aspect herein, a process is provided for hydrolysing or preferably neutralising water-absorbing cross-linked polymers in ester or preferably acid (respectively) form in a supercritical medium (as described herein), to obtain the salt form of said water-absorbing cross-linked polymers; hereby the optional and preferred process and product features as described herein above and below can be equally employed. Thus, in some aspect, a process is provided for making water-absorbing cross-linked polyelectrolyte polymers, being at least partially in salt form, comprising the steps of:

i) obtaining a water-absorbing cross-linked polymer of polymerized monomers in acid and/or ester form;

ii) obtaining a fluid comprising or consisting of a supercritical medium;

iii) obtaining a neutralizing agent or hydrolizing agent;

iv) combining the polymers of i) and said medium of ii) and said agent of iii), to obtain said water-absorbing cross-linked polyelectrolyte polymers in salt form, whereby for example prior to step i), said process has the steps of:

a) obtaining polymerizable monomers in acid or ester form;

b) obtaining a fluid, comprising or consisting of one or more supercritical medium/media;

c) obtaining a polymerization initiator;

d) obtaining a cross-linking compound;

e) combining the polymerizable monomers of a) and said supercritical medium of b) and a polymerization initiator of c) and said cross-linking compound of d), thereby polymerizing said polymerizable monomers to form polymers and cross-linking said polymers, to form water-absorbing cross-linked polymers;

whereby in step ii) said medium or fluid may optionally be the medium or fluid of step e).

Thus, in another embodiment of the invention, a process is provided whereby water-absorbing cross-linked polymers in acidic form, as described herein, are neutralized with a neutralization agent, as described herein above, to obtain partially or completely neutralized water-absorbing cross-linked polymers, as described herein (in the form of the salt thereof, for example), and extracting the neutralization agent there from by use of a supercritical medium, as described herein.

In some embodiment, the step h) above may alternatively be used to (partially) neutralize the obtained polymer with a neutralization agent, including a solvent, e.g. in an organic solvent such as aqueous ethanol. Then, in a further step, the neutralization solvent may then be removed, e.g. by submitting this to a supercritical medium extraction, as describe herein (also to recuperate/recycle the solvent).

DETAILED DESCRIPTION OF THE INVENTION

The water-absorbing cross-linked polymers of the inventions absorb water; they are typically water-swellable when absorbing water, and typically hydrogel-forming when absorbing water; these polymers may also absorb other liquids e.g. and thereby swell. Thus, when used herein, 'water-absorbent', or 'water-swellable' means that the polymers swell at least in water, but typically also in other liquids or solutions, preferably in water based liquids such as 0.9% saline, urine etc.

Typically, the water-absorbing cross-linked polymers absorb at least 10 g/g of saline solution, preferably at least 15 g/g, as measured under the Standard Test WSP 241.2 "Fluid Retention capacity in Saline, after Centrifugation".

In the first embodiment of the invention, the water-absorbing cross-linked polymer according to this invention is formed from polymerizable monomers in the presence of a polymerization initiator, and in the presence of a cross-linking compound, capable of cross-linking the polymers.

Any suitable polymerizable monomer can be used, as described below; in some preferred embodiment herein the monomers include or consists of acrylic acid and/or acrylate salts; in some embodiment herein, preferably including at least acrylate salts. Any suitable polymerization initiator can be used, such as for example those described below. Any suitable cross-linking compound can be used, including for example those below.

In the first aspect of this invention, this polymerization is done in the presence of a supercritical medium (or: fluid) comprising at least a primary supercritical medium (or: fluid), for example supercritical carbon dioxide, and optionally other fluids or supercritical secondary medium (media), such as polar fluid(s) or polar secondary supercritical medium (media) such as for example supercritical water, supercritical alcohol, such as supercritical methanol, supercritical ketone, for example supercritical acetone, or mixtures of any fluids or said supercritical media.

In some embodiment herein, the water-absorbing cross-linked polymers have acid functions; in some other embodiments herein, said acid functions of said polymers are typically at least partially neutralized, also referred to as water-absorbing cross-linked polyelectrolyte polymers.

In a further aspect of the present invention, the water-absorbing cross-linked polymers have acid functions and/or ester functions, and said polymers are hydrolyzed or neutralized in the presence of a supercritical medium, as described herein, to result in water-absorbing cross-linked polyelectrolyte polymers that are at least partially in their salt form, e.g. sodium salt form. Such polyelectrolytes have typically an improved absorbency performance for e.g. urine, compared to the acid forms; however traditional method using aqueous solutions to hydrolyze of neutralize such polymers with ester or typically acid groups require subsequent energy-intensive drying steps. The process of the invention using supercritical medium however requires much less energy.

The water-absorbing cross-linked polymers made by the process of the invention may be in acid form, and then they may be neutralized or partially neutralized in a subsequent process step, by use of a neutralizing system or agent; this may be done in a supercritical medium, or this may be done by conventional methods, involving for example an organic liquid, optional mixed with water.

Especially preferred are carboxylic acid polymers, which contain a multiplicity of as carboxylic acid functional groups, formed from monomers with one or more carboxylic acid group; in some embodiments herein, the monomer or part thereof may be in the form of a carboxylate salt, preferably sodium salts, as described below.

Thus, the polymerizable monomers may preferably be polymerizable acid-containing monomers, e.g. carboxylic acid-containing monomers, or monomers containing functional groups which can be converted to acid groups after polymerization, e.g. esters and anhydrides, and mixtures thereof.

In other embodiments, the polymerizable monomers may preferably include or may be salts of polymerizable acid-containing monomers, e.g. carboxylate-containing monomers.

In some other embodiments herein, the water-absorbing cross-linked polymers are polyelectrolytes, e.g. cationic or anionic, e.g. neutralized or partially neutralized carboxylate-containing polymers.

Some polymerizable non-acid monomers can also be included, usually in minor amounts, in preparing the water-absorbent cross-linked polymers herein. Such non-acid monomers can include, for example, monomers containing the following types of functional groups: carboxylate or sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

Olefinically unsaturated carboxylic acid (or derivates) or salts thereof useful herein include the acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and/or each of the salts thereof, and/or maleic anhydride. Acrylic acid may in some embodiments be most preferable. In other embodiments, acrylate salts or mixtures of acrylate salts and acrylic acid may be used. In such instances, the supercritical medium may comprise for example a polar supercritical medium, e.g. secondary medium, and/or a polar liquid.

The water-absorbing polymers are cross-linked, i.e., the polymerization is carried out in the presence of a cross-linking system comprising or consisting of one or more compounds having two or more functional groups that can link two or more polymers. For example, for polymers with carboxyl groups, such as polyacrylates/polyacrylic acids, the cross-linking compound may be a non radical cross-linking compound having two or more functional groups each of which allows formation of an ester or an amide bond by reaction with carboxyl groups of the polymers, e.g. di-epoxides.

Suitable levels, in order to achieve suitable levels of cross-linking, may for example be from at least 0.01 mol % or from at least 0.05 mol % or at least 0.1 mol %, to for example 5 mol %, or to 2 mol % or to 1 mol % (percentage based on monomer level).

The cross-linking compound may have functional groups that are polymerizable groups which can be polymerized e.g. by a free-radical chain polymerization mechanism, to the polymers. Useful crosslinkers may for example be ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in German patent application 103 31 450.4, mixed acrylates which, as well as acrylate groups, comprise further ethylenically unsaturated groups, as described in German patent applications 103 31 456.3 and 103 55 401.7, or crosslinker mixtures as described for example in DE-A 195 43 368, DE-A 196 46 484, WO 90/15830 and WO 02/32962. Useful crosslinkers may include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl esters and vinyl esters of di-, tri- or polycarboxylic acids for example tartaric acid, citric acid, adipic acid like triallylcitrate and divinyladipate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A 343 427. Useful crosslinkers ii) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention utilizes di(meth)acrylates of polyethylene glycols, the polyethylene glycol used having a molecular weight between 300 and 1000.

However, particularly advantageous crosslinkers ii) are di- and triacrylates of altogether 3- to 15-tuply ethoxylated glycerol, of altogether 3- to 15-tuply ethoxylated trimethylolpropane, especially di- and triacrylates of altogether 3-tuply ethoxylated glycerol or of altogether 3-tuply ethoxylated trimethylolpropane, of 3-tuply propoxylated glycerol, of 3-tuply propoxylated trimethylolpropane, and also of altogether 3-tuply mixedly ethoxylated or propoxylated glycerol, of altogether 3-tuply mixedly ethoxylated or propoxylated trimethylolpropane, of altogether 15-tuply ethoxylated glycerol, of altogether 15-tuply ethoxylated trimethylolpropane, of altogether 40-tuply ethoxylated glycerol and also of altogether 40-tuply ethoxylated trimethylolpropane.

The acid groups of the monomers or of the cross-linked polymers useful herein obtained are for example neutralized to a degree from 25 mol % to 90 mol %, or for example from 50 mol % to 80 mol %. This may be done by any means, e.g. by addition of a base. In one aspect of the present invention, this is done in the presence of a supercritical medium (and for example in the absence of water).

In some particular preferred embodiment the acid groups of the monomers or the cross-linked polymers obtained are preferably more than 60 mol %, more preferably more than 61 mol %, even more preferably more than 62 mol % and most preferably more than 63 mol % and preferably not more than 70 mol %, more preferably not more than 69 mol %, even more preferably not more than 68 mol % and most preferably not more than 67 mol % neutralized. This may be done during polymerization and cross-linking or subsequent thereto. This may be done in the supercritical medium described herein, or this may be done as an additional step in conventional liquids, such as an alcohol or an alcohol with water (e.g. small amounts, e.g. less than 40 vol %, or less than 30 vol %). The subsequent extraction of the neutralization fluid maybe done by use of a supercritical medium, as described herein.

Thus, in another embodiment of the invention, a process is provided whereby water-absorbing cross-linked polymers in acidic form, as described herein, are neutralized with a neutralization agent, as described herein, to obtain partially or completely neutralized water-absorbing cross-linked polymers, as described herein (in the form of the salt thereof, for example), and extracting the neutralization agent there from by use of a supercritical medium, as described herein.

In some embodiments, organic neutralizing agents may be used. Suitable agents include ethanolamine, diethanolamine, triethanolamine or dimethylaminoethanolamine, and/or alkali metal (e.g. sodium) hydroxides, alkali metal oxides, alkali metal carbonates or alkali metal bicarbonates and also mixtures thereof, may be used (in which case sodium and potassium are particularly preferred as alkali metals, but most preference is given to sodium hydroxide, sodium carbonate or sodium bicarbonate and also mixtures thereof), in particular when a secondary (e.g. more polar) liquid(s) or medium (media) is present, or when the neutralization step is done as a separate step, without supercritical medium, e.g. in conventional liquids.

Thus, neutralization may be achieved by admixing the neutralizing agent as a solid material, or as a solution in a supercritical medium, or in another liquid (solvent).

In some embodiment, a solution of the neutralization agent, even in water, may be brought in contact with the mixture via a membrane that allows electrolytes to pass but not the solvent, e.g. water. For example, alkali metal (e.g. sodium) hydroxides, alkali metal oxides, alkali metal carbonates or alkali metal bicarbonates and also mixtures thereof, may be used in this manner.

Neutralization can be carried out after polymerization and cross-linking, but it is alternatively, or also possible to neutralize, for example up to 40 mol %, or for example from 10 to 30 mol % or for example from 15 to 25 mol % of the acid groups before polymerization by adding a portion of the base/neutralizing agent to the monomer solution and to set the desired final degree of neutralization only after polymerization.

The water-swellable polymers may have a low amount of extractables, preferably less than 15% (by weight of the polymers), more preferably less than 10% and most preferably less than 5% of extractables, or even less than 3% (values of 16 hour test). The extractables and levels thereof and determination thereof is further described in for example U.S. Pat. No. 5,599,335; U.S. Pat. No. 5,562,646 or U.S. Pat. No. 5,669,894.

Initiator systems or initiator(s) that may be added, either simultaneously with the cross-linking system and monomers, or as separate, e.g. subsequent step, include for example one or more of the following.

Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide and tert-amyl perneodecanoate. Preferred azo compounds include 2,2'-azobisisobutyronitrile, 2,2'-azobis (2,4-dimethylvaleronitrile) and 2,2'-azobis(4-methoxy-2,4-dimethyl-valeronitrile), especially water-soluble azo initiators, examples being 2,2'-azobis-{2-[1-(2-hydroxyethyl)-2-imidazolin-2-yl]propane}dihydrochloride, 2,2'-azobis-(2-amidinopropane)dihydrochloride, 2,2'-azobis[2-(2-imidazolin-2-yl)propane]dihydrochloride and 2,2'-azobis[2-(5-methyl-2-imidazolin-2-yl)propane]dihydrochloride. Very particular preference is given to 2,2'-azobis[2-(2-imidazolin-2-yl)propane]dihydrochloride and 2,2'-azobis[2-(5-methyl-2-imidazolin-2-yl)propane]dihydrochloride. Preferred may be persulfates such as sodium peroxodisulfate, potassium peroxodisulfate and ammonium peroxodisulfate; hydroperoxides such as t-butyl hydroperoxide and cumene hydroperoxide; and azo compounds such as 2,2'-azobis-2-amidinopropane hydrochloride, e.g. such as VA-044, V-50 and V-501 (all manufactured by Wako Pure Chemical Industries Ltd.), and mixtures of $Fe^{2+}$; and hydrogen peroxide, or hydrogen peroxide and ascorbic acid. The latter may be a preferred initiator system for use herein.

The polymerization initiator may be used per se, and then it may for example be added to the supercritical medium with polymerizable monomers or it may be used as a dispersion or solution. It may then be preferred that it is added in the form of a dispersion/solution in a liquid, which may be a supercritical medium.

In one embodiment, a mixture of two or more polymerization initiators is used, for example one of the class of azo-compounds and one of the class of peroxo or peroxide compounds, as described above. This is believed to ensure fast polymerization.

In order to increase the polymerization speed, the polymerization initiator may for example be introduced onto the polymerization reaction liquid at a level of for example at least 0.1% by weight of the polymerizable monomers, or for example at least 0.3% or at least 0.5% or at least 0.7%, up to typically 10% or 5% or 3% by weight.

The polymerization rate can be controlled through the temperature and the identity and amount of the initiator system used. As for example described in US2008/242817, the use of azo compound initiator or redox initiators is advantageous for directing the rate of polymerization.

For some initiators, no activation is needed; other initiators may require activation, as known in the art. The initiator may be activated by any method known in the art, including heat or radiation. Thereto, it may be preferred that the dispersions/solutions of the monomer compound are cooled (e.g. to a temperature of less than polymerization temperature, e.g. less than 20° C., or less than 10° C.) or and/or shielded from radiation prior to introduction of the initiator, and optionally at the moment of addition of the initiator, and that said combination of initiator and dispersion/solution is exposed to the activation source, e.g. heat, radiation, only at the desired moment.

A polymerization catalyst may also be present, such as for example TMEDA, N,N,N',N' tetramethylethylenediamine.

The process may comprise additional step or steps of for example: surface cross-linking the surface of the polymer particles, coating the polymer particles, or combinations thereof. This may be done by any conventional method, after removal of the supercritical medium, e.g. via obtaining its gaseous state and removing this.

In some embodiments, the combination of the components, optionally in the initiator system being added in a subsequent step, is done in a first reactor or reactor section, and then the polymerization and cross-linking is continued in a second reactor or reactor section, (optionally by adding then the initiator system in that reactor or reactor section). This may be for example a tube reactor with multiple reactor sections. It may also be a first reactor with a relaxation nozzle(s), leading to a further vessel, whereby the polymerization and cross-linking can take place in the nozzle(s) and where the supercritical medium is present during the reaction, but becomes gaseous during the flow through said nozzle, to result in a polymerized and cross-linked polymer, without the supercritical fluid, e.g. in particulate form.

The process of the invention may take place by means of transfer through an extruder, spray head or nozzle(s) of the mixture to a reactor with a reduced pressure (including ambient) to allow expansion of the supercritical medium, to allow it to become gaseous. This gaseous phase can then be removed and recycled into supercritical medium, if desired and reused for the process herein.

The process herein may be such that the resulting water-absorbing cross-linked polymers are in particulate form. The particle size of the particles may be controlled such that the mass median particle size up to 1 mm, or even between 10 microns and 1 mm, or preferably between 50 µm and 800 µm, as can for example be measured by the method set out in for example EP-A-0691133.

In one embodiment of the invention, at least 80% by weight of the particles have particle sizes between 10 µm and 1200 µm or even between 50 µm and 800 µm and a mass median particle size between 100 or 200 and 800 µm or 600 µm.

In some aspect, a process is provided for making water-absorbing cross-linked polyelectrolyte polymers, being at least partially in salt form, comprising the steps of:

v) obtaining a water-absorbing cross-linked polymer of polymerized monomers in acid and/or ester form;

vi) obtaining a fluid comprising or consisting of a supercritical medium;

vii) obtaining a neutralizing agent or hydrolyzing agent;

viii) combining the polymers of i) and said medium of ii) and said agent of iii), to obtain said water-absorbing cross-linked polyelectrolyte polymers in salt form, whereby for example prior to step i), said process has the steps of:

f) obtaining polymerizable monomers in acid or ester form;

g) obtaining a fluid, comprising or consisting of one or more supercritical medium/media;

h) obtaining a polymerization initiator;

i) obtaining a cross-linking compound;

j) combining the polymerizable monomers of a) and said supercritical medium of b) and a polymerization initiator of c) and said cross-linking compound of d), thereby polymerizing said polymerizable monomers to form polymers and cross-linking said polymers, to form water-absorbing cross-linked polymers;

whereby in step ii) said medium or fluid may optionally be the medium or fluid of step e).

Thus, in another embodiment of the invention, a process is provided whereby water-absorbing cross-linked polymers in acidic form, as described herein, are neutralized with a neutralization agent, as described herein above, to obtain partially or completely neutralized water-absorbing cross-linked polymers, as described herein (in the form of the salt thereof, for example), and extracting the neutralization agent there from by use of a supercritical medium, as described herein.

Supercritical Medium

When a gas is compressed to a sufficiently high pressure, it becomes liquid. If, on the other hand, the gas is heated beyond a specific temperature, it can no longer be transferred to the liquid state by compression. This temperature is called the critical temperature and the corresponding vapor pressure is called the critical pressure. These values of temperature and pressure define a critical point, which is unique to a given substance. The state of the substance is called supercritical state and the substance is then a supercritical medium or fluid.

For a mixture, it represents the condition at which specific properties of the gas and liquid phases in equilibrium become identical. A supercritical fluid possesses approximately the penetration properties of a gas simultaneously with the solvent properties of a liquid For example, the critical temperature and pressure values for carbon dioxide are 31.1° C. and 73.8 bar. For propane, the critical temperature and pressure values are 38.8° C. and 42.5 bar.

The supercritical medium (or: fluid) takes on many of the properties of both gas and liquid. In the supercritical state, increasing the solvent capacity and varying the solvent properties can be achieved with relatively small changes in temperature and pressure.

For the present invention the supercritical medium may be supercritical carbon dioxide, $CO_2$.

As mentioned above, the medium may comprise mixtures of supercritical materials, for example having a primary supercritical medium, such as supercritical $CO_2$, and a secondary supercritical medium that aids solution of one or more of the reaction components or reaction products. Also liquids that are not supercritical can be added to the medium herein.

Thus, mixtures of fluids (e.g. liquids, not being in supercritical state) and one or more supercritical medium or media may be used. In some embodiments herein, the medium used in the processes of the invention comprises at least 50% by weight, or at least 60% or at least 70% by weight of supercritical fluid $CO_2$.

$CO_2$'s near ambient critical temperature makes it ideally suitable for the present processes, to reduce the energy requirement related to increased temperatures. Due to its very low latent heat of vaporization, relatively low energy input is required for the removal of the $CO_2$ after the desired polymers are formed. Furthermore the energy required for attaining the supercritical state of $CO_2$ is minimal. $CO_2$ required for the supercritical fluid extraction process is readily available, as it is e.g. obtained as a by-product from the fermentation process or fertilizer industry.

The process steps of the present inventions can be performed in any reactor that is pressure resistant and not in air communication with the environment. Furthermore, it may comprise a device, such as a pump, which maintains constant flow-rate and pressure of the supercritical fluid within the vessel. All components are typically combined in a closed system.

In some embodiments herein, the polymerization step takes place in a first reactor with a first pressure and the resulting polymers or cross-linked polymer and the supercritical medium transfer, e.g. subsequently, to a second vessel with a second pressure, which is less than the first pressure, for example at least 40% less, or at least 50% less, or for example ambient pressure, whereby the supercritical fluid becomes a gas, e.g. $CO_2$, that can then leave the second vessel and that optionally can be recycled, by submitting it to increased pressure, forming thereby the supercritical medium, (and using it again in the polymerization process step (or hydrolysis or neutralization step)). This may be done via one or more nozzles or one or more spray heads, connected to said first vessel, where through said the supercritical medium and said polymers or cross-linked polymers is allowed to flow, into said second vessel with reduced pressure. The supercritical medium becomes gaseous, leaving the water-absorbing cross-linked polymers, for example in particulate form, e.g. having a specific particle size depending on dimensions (diameter) size of the orifices of the nozzles or spray heads. The particle size of the particulate water-absorbing cross-linked polymers can thereby be controlled by selected specific nozzle and spray head dimensions, orifices dimensions, and other process conditions, such as flow rate and temperature and pressure.

The supercritical medium evaporates upon reduced pressure very rapidly, including the supercritical medium in the interior of said polymers. Due to this quick expansion, pores or channels can be formed in said cross-linked polymer particles herein.

Valves on the first and second vessel may serve to control introduction of the monomers, initiator, cross-linking compound, supercritical fluid, and base, when used. Optionally, the vessel(s) may further comprise cooling or heating element(s), e.g. to maintain the supercritical fluid at the desired temperature.

As higher pressures are more difficult to facilitate, relatively low pressures are desirable from a process engineering and cost standpoint, provided the supercritical fluid is at its supercritical state. In the processes of the present invention, the supercritical fluid may be under a pressure of from 80 bar or from 100 bar, or from 120 bar, to for example 400 bar, or to 350 bar or to 250 bar.

As carbon dioxide reaches its supercritical state at a pressure of 73.8 bar and at a temperature of 31.1° C., the temperature of the supercritical fluid then be for example be at least 35 or at least 40° C. Temperatures below 40° C. may result in areas within the system having a temperature which is at least temporarily below the supercritical temperature of 31.1° C. Thus, to ensure process stability, the temperature should be at least 40° C. Or for example, if propane is used as supercritical fluid (or a mixture which predominantly consists of propane), it may be desirable to have a temperature of at least 45° C. due to the slightly higher critical temperature of propane compared to carbon dioxide. Generally, it is desirable that the temperature of the supercritical fluid is from 40° C. to 150° C., or to 120° C., or to 100° C., or to 80° C. or to 60° C.

Alternatively the reaction could be done within tube or pipe reactors with different pressure and/or temperature settings along the pipe and along the flow of the supercritical medium and/or mixture, to control the polymerisation and cross-linking, and removal of the supercritical medium.

Absorbent Articles

The water-absorbing cross-linked polymers obtainable by the processes of the invention are useful in absorbent articles, i.e. devices that absorb and retain liquids (such as blood, menses and urine), and more specifically, devices that are placed against or in proximity to the body of the wearer to absorb and contain the various exudates discharged from the body. Absorbent articles include, but are not limited to, diapers (including diapers with fasteners, training pants, adult incontinence diapers and adult incontinence pants), adult incontinence briefs, diaper holders and liners, feminine hygiene articles, including sanitary napkins, panty-liners and the like. Diaper refers to an absorbent article generally worn by infants and incontinent persons about the lower torso; infant diaper refers to baby and toddler diapers, including training pants, worn about the lower torso.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making water-absorbing cross-linked polymers comprising the steps of:
   a) obtaining polymerizable monomers;
   b) obtaining a supercritical reaction medium;
   c) obtaining a polymerization initiator system;

d) obtaining a cross-linking system;
e) combining the polymerizable monomers of step a) and the supercritical reaction medium of step b), the cross-linking compound of step d), and (simultaneously or subsequently) the polymerization initiator system of step c), to form a mixture; and
f) polymerizing the polymerizable monomers to form polymers and cross-linking the polymers;
to form water-absorbing cross-linked polymers; wherein step f), or steps e) and f), are done in a first reactor or reactor section with a first pressure;
g) transferring the water-absorbing cross-linked polymers and supercritical medium of step f) to a second reactor or second reactor section that has a second, reduced pressure to obtain water-absorbing cross-linked polymers, and a gaseous phase of the supercritical medium, or part thereof; and
h) separating the gaseous phase from the water-absorbing cross-linked polymers;
wherein the water-absorbing cross-linked polymers obtained in step f) are in articulate form; and wherein the transfer in step g) to the second reactor or reactor section is done via one or more spray heads or nozzles.

2. The process according to claim 1, wherein the gaseous phase separated in step h) is submitted to an increased pressure to form a supercritical medium and recycled to a subsequent step b).

3. The process according to claim 1 further comprising the steps of:
  i) obtaining a neutralizing system; and
  j) combining the neutralizing system with the other components in step e), to form a mixture.

4. The process according to claim 1, wherein the supercritical medium comprises supercritical $CO_2$.

5. The process according to claim 1, wherein the supercritical medium comprises supercritical $CO_2$ as a primary supercritical medium, and a polar secondary medium.

6. The process according to claim 5, wherein the polar secondary medium is selected from the group consisting of liquid alcohol, liquid ketone, water, and combinations thereof.

7. The process according to claim 5, wherein the polar secondary medium is in the supercritical state.

8. The process according to claim 7, wherein the polar secondary medium is selected from the group consisting of supercritical alcohol, supercritical ketone, supercritical water, and combinations thereof.

9. The process according to claim 1, wherein the monomers include acrylic acid and/or acrylate salt.

10. The process according to claim 1, wherein the weight ratio of the polymerizable monomers to the supercritical medium is less than about 1:2.

11. The process according to claim 1, wherein the initiator system comprises one or more initiator compounds, being present at a total mol % (of monomer level) of from about 0.05% to about 2%.

12. The process according to claim 1, further comprising the steps of:
  m) separating the supercritical medium and the water-absorbing cross-linked polymers;
  n) post-treating the water-absorbing cross-linked polymers by one or more steps selected from the group consisting of surface-cross-linking the polymers, and coating the polymers.

13. The process according to claim 12, wherein the water-absorbing cross-linked polymers being post-treated in step n) are in particulate form.

14. A process for making water-absorbing cross-linked polymers comprising the steps of:
  a) obtaining polymerizable monomers;
  b) obtaining a supercritical reaction medium;
  c) obtaining a polymerization initiator system;
  d) obtaining a cross-linking system;
  e) combining the polymerizable monomers of step a) and the supercritical reaction medium of step b), the cross-linking compound of step d), and (simultaneously or subsequently) the polymerization initiator system of step c), and
  f) polymerizing the polymerizable monomers to form polymers and cross-linking the polymers wherein the process further comprises the steps of:
  to form water-absorbing cross-linked polymers;
  g) obtaining a neutralizing system; and
  h) combining the neutralizing system with the other components in step e), to form a mixture.

15. A process for making water-absorbing cross-linked polymers comprising the steps of:
  a) obtaining polymerizable monomers;
  b) obtaining a supercritical reaction medium;
  c) obtaining a polymerization initiator system;
  d) obtaining a cross-linking system;
  e) combining the polymerizable monomers of step a) and the supercritical reaction medium of step b), the cross-linking compound of step d), and (simultaneously or subsequently) the polymerization initiator system of step c), to form a mixture;
  f) polymerizing the polymerizable monomers to form polymers and cross-linking the polymers;
  to form water-absorbing cross-linked polymers; wherein step e) is done in a first reactor or reactor section with a first pressure wherein the process further comprises the steps of:
  g) transferring the mixture of step e) to a second reactor or second reactor section that has a second, reduced pressure, and performing step f) to obtain water-absorbing cross-linked polymers, and gaseous phase of the supercritical medium, or part thereof; and
  h) separating the gaseous phase from the water-absorbing cross-linked polymers.

16. The process according to claim 15, wherein step e) is performed in the absence of the polymerization initiator system obtained in step c), and the polymerization initiator system is added to the mixture of step e) in the second reactor or second reactor section, in step g).

17. The process according to claim 15, wherein the water-absorbing cross-linked polymers obtained in step f) are in particulate form.

18. The process according to claim 15, wherein the transfer in step g) to the second reactor or reactor section is done via one or more spray heads or nozzles.

19. The process according to claim 15, wherein the gaseous phase separated in step h) is submitted to an increased pressure to form a supercritical medium and recycled to a subsequent step b).

* * * * *

UNITED STATES PATENT AND TRADEMARK OFFICE
CERTIFICATE OF CORRECTION

PATENT NO. : 9,006,366 B2  
APPLICATION NO. : 13/285058  
DATED : April 14, 2015  
INVENTOR(S) : Thomas Tombuelt-Meyer et al.

Page 1 of 1

It is certified that error appears in the above-identified patent and that said Letters Patent is hereby corrected as shown below:

In the claims

Column 13, line 21, delete "articulate" and insert -- particulate --.

Signed and Sealed this
First Day of December, 2015

Michelle K. Lee
*Director of the United States Patent and Trademark Office*